United States Patent
Chhatwal et al.

(10) Patent No.: US 8,530,224 B2
(45) Date of Patent: Sep. 10, 2013

(54) **MARKER OF *STREPTOCOCCUS ANGINOSUS/STREPTOCOCCUS CONSTELLATUS* (MOAC) AND USES THEREOF**

(75) Inventors: Gursharan S. Chhatwal, Denkte (DE); Patric Nitsche-Schmitz, Braunschweig (DE); Silvana Reissmann, Braunschweig (DE)

(73) Assignee: Helmholtz-Zentrum für Infektionsforschung GmbH, Braunschweig (DE)

( * ) Notice: Subject to any disclaimer, the term of this patent is extended or adjusted under 35 U.S.C. 154(b) by 86 days.

(21) Appl. No.: 12/995,052

(22) PCT Filed: Jun. 18, 2009

(86) PCT No.: PCT/EP2009/004416
§ 371 (c)(1),
(2), (4) Date: Nov. 29, 2010

(87) PCT Pub. No.: WO2009/153046
PCT Pub. Date: Dec. 23, 2009

(65) Prior Publication Data
US 2012/0087930 A1    Apr. 12, 2012

(30) Foreign Application Priority Data
Jun. 19, 2008  (EP) .................................. 08011200

(51) Int. Cl.
*C12N 1/20* (2006.01)
*C12Q 1/68* (2006.01)
*C12P 21/06* (2006.01)

(52) U.S. Cl.
USPC ........ 435/252.3; 435/6.1; 435/6.12; 435/69.1; 435/810

(58) Field of Classification Search
None
See application file for complete search history.

(56) References Cited

U.S. PATENT DOCUMENTS
6,054,269 A    4/2000  Garnier et al.
7,482,117 B2 *  1/2009  Cargill et al. ................ 435/6.14

FOREIGN PATENT DOCUMENTS
WO    WO 01/48208       7/2001
WO    WO 2006/069200    6/2006
WO    WO 2007/018563    2/2007

OTHER PUBLICATIONS

Bartie et al., "Macrorestriction fingerprinting of "*Streptococcus milleri*" group bacteria by pulsed-field gel electrophoresis," *Journal of Clinical Microbiology*, Jun. 2000, pp. 2141-2149, vol. 38, No. 6.
Chen et al., "Identification of clinically relevant viridans streptococci by an oligonucleotide array," *Journal of Clinical Microbiology*, Apr. 2005, pp. 1515-1521, vol. 43, No. 4.
Database EMBL [Online], "Sequence ID No. 15352 from WO 2006/069200", Jun. 29, 2006, XP002546003, retrieved from EB, database accession No. AES88683.
Nikolaitchouk et al., "The lower genital tract microbiota in relation to cytokine-, SLPI- and endotoxin levels: application of checkerboard DNA—DNA hybridization (CDH)," *AMPIS*, 2008, pp. 263-277, vol. 116, No. 4.
Siqueira et al., "*Actinomyces* species, Streptococci, and *Enterococcus faecalis* in primary root canal infections," *Journal of Endodontics*, Mar. 2002, pp. 168-172, vol. 28, No. 3.
Takao et al., "Identification of the anginosus group within the genus *Streptococcus* using polymerase chain reaction," *FEMS Microbiology Letters*, 2004, pp. 83-89, vol. 233, No. 1.
Tung et al., "Array-based identification of species of the genera *Abiotrophia, Enterococcus, Granulicatella,* and *Streptococcus*," *Journal of Clinical Microbiology*, Dec. 2006, pp. 4414-4424, vol. 44, No. 12.
Waterhouse et al., "Dispensable genes and foreign DNA in *Streptococcus mutans*," *Microbiology*, 2006, pp. 1777-1788, vol. 152, No. Part 6.

* cited by examiner

*Primary Examiner* — Padma V Baskar
(74) *Attorney, Agent, or Firm* — Saliwanchik, Lloyd & Eisenschenk

(57) ABSTRACT

The present invention relates to nucleic acids, vectors and polypeptides that are suitable markers for detecting *Streptococcus* strains of the *anginosus* group, preferably for detecting *Streptococcus anginosus* and/or *Streptococcus constellatus* as well as for discriminating *Streptococcus anginosus* and/or *Streptococcus constellatus* from other streptococci. The present invention furthermore relates to these nucleic acids and polypeptides for use in the diagnosis and/or prognosis of infections with *Streptococcus* strains of the *anginosus* group. The present invention furthermore relates to methods utilizing these nucleic acids and polypeptides as well as to arrays and antibodies.

12 Claims, 1 Drawing Sheet

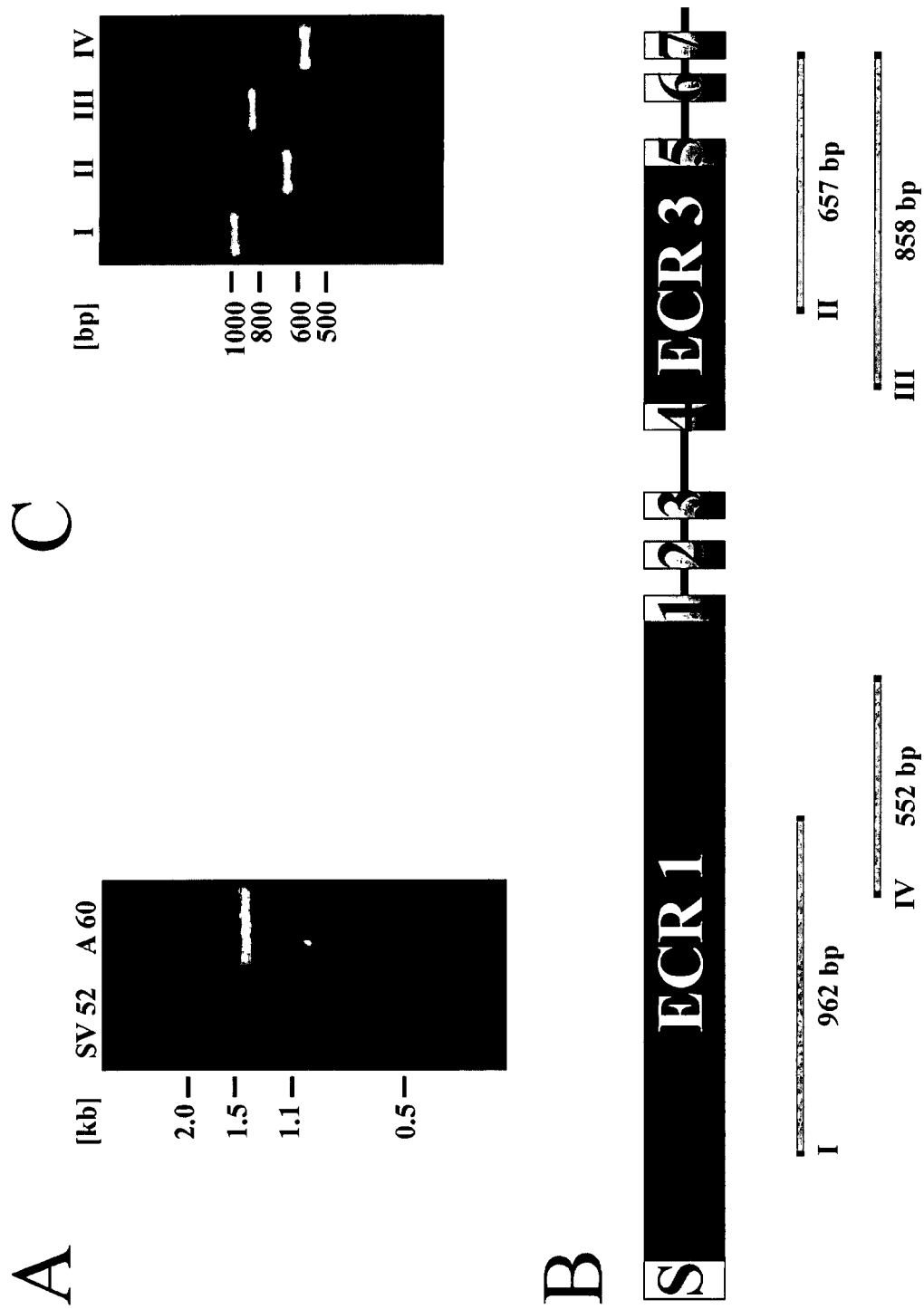

SEQUENCE LISTING

<160> NUMBER OF SEQ ID NOS: 27

<210> SEQ ID NO 1
<211> LENGTH: 3369
<212> TYPE: DNA
<213> ORGANISM: Streptococcus anginosus

<400> SEQUENCE: 1
atgaaaaaat ccattctaaa taaggatatc tggctctctt ttcgtcagtc caaaggacgc    60

```
tttctgtcca ttatgttttt gatgatgtta ggttcttttg cgctagtagg actgaaagca    120
gccagtccag acattgaaaa ttcagccaat cgttatcttt cacagatgaa aatgatggat    180
ttggcagtga tgtcagatta tggtatcagc aaagctgacc aaaaagaact gaatgcagtt    240
ccaaatgcac aggtagaata tggttatttt acagatacgg tgattggaga tagttcaact    300
tctgttcgag ttttttctca gacaactaat atttccaagt tcaagcttgt ttcaggtcat    360
tttccaagca aggaaaatca agtggttttg gctagttttt atcaaggaaa gtacaagatt    420
ggcgatagca ttactttaaa cgaggaagga accaatgatt atgctttgaa gcagcatacc    480
tttacggtga cgggattcgt caattcaagt gaattggctt cgacgatttc tcttggcaat    540
tctaactcag ggagtgggac cttatctgct tatgcagtgg tgatgccaaa aacatttcaa    600
agttcagtct atacagttgc tcgtttgaag tatgacgatt taaaaacact taattctttt    660
ggagactcct atcgaaaaaa ggtaaaacgg tatgaaaatg agctggaaaa gctagtggct    720
gataatggga aaaatcgttt atcagagata aaaaacaag cacagacaaa aattgcggac    780
ggagaagcaa aaattcaaac ttctcaacaa gcattggcag atgcccagca gcaactaagg    840
aatgcgcagg atcaaattga tcaaaaaaga gcagatttag aggctgccca aggtcagata    900
actgaaaaag aaagcttgct tgcgcaagga gctactcaaa ttgcacaggc tgagcagact    960
ttggaaaata cgaaagaaaa attagataca gccgccgctc aactgtcttc aggttgggca    1020
caattgaacc aaacgaaaac ccaattagat caggcagcta gtcaattatc tgctgcaaaa    1080
gaaaatgtaa caaatgctca agctacatta gctacgcgc aggcagaatt ggaaaaaggt    1140
caagttcaat tagcagcagc taaagtggat ttgcagaaaa aaatgaccgc gcttcaagca    1200
caaggaattg attcagcaac agtgcctgaa attgtggcag cacaaactca actagcacaa    1260
gaagaagcaa aattaaatct tgtccgtaca gaactggaga aaaagcaggc tgaatttcaa    1320
actggactgt cgcagtacaa aagccaagaa gcgctttatc aagcaggact tgcccaatac    1380
caatctgcgg ctgagacatt gaatgcgaaa caagctgaat atgacgcagg cttagctcaa    1440
tatcaaagtg gtcaggcaac cttaagaaat aaacaagccg agtaccaagc aggtcaagcc    1500
caattggcgc aagcaaaaca acaaatcgca gacggtcagg cgcaattgga ccaagctcag    1560
gcaacattga acgataaaaa aactgaatac gaaaagcaaa agaaagatgc tgaaacaaaa    1620
ataaaaaatg ggcaagcaga cattcaaaag gcaaagagg aagtagctgg tttgtctgta    1680
ccaacctacc gtgtgtatac acgtcggaca tttccaggag ctgacgagta cacaacaacg    1740
gggaatcgtg cttatggaat ctcagctgta ggaaatgctt ttccgattgt actatatctg    1800
gtagctgccc ttgtaacggt aacgacaatg acacgttttg tcagcgaaga acgcacaaat    1860
gctggcgttt taaaagcttt aggttatcgg aatcaagatg tcgttaagaa atttgtcgtt    1920
tatggcttgg tttcaagttt gttaggtaca gtaatgggaa gtttgttagg tacttatttc    1980
ttaccctaca tcttagggaa aactattttt aagacatcaa cttatccaga tttgcgatta    2040
gaattttatt gggaaattag tctcattgct ctttttatgct cggtcttgtg tggtgtcgca    2100
ccagcccttt atattgctca caaagagttg aaagaaaaac catctcaatt attgttgccc    2160
aaggcaccta ccaaaggctc aaaaatcttg ctagagcgga ttgacttcat ttggcgtcga    2220
ctcagctttg cgcaaaaagt gacggctcga aatatctttc gttacaagca agaatgctg    2280 atgaccattt ttggtgtggc aggctccgtc gccctcttat tgccggtttt ggggatgtct    2340
tcttccatgg aaggtatggg aaatcggcag tatgagaaaa ttatcaaata cgatgcggtc    2400
atttcgcaaa aacagcatct caaatcagac gagcaagcag caatcaatca tttattagca    2460
```

```
gataaaaaaa tagctaaaaa gcacggtatt tatcaagaaa catttaccaa aaaaattaaa    2520
ggagcaaaag atgaacaatc tctcgcgtta tttgtgacaa caggcaagga ttttatcat     2580 ttcatagagt tatatgatag tcaaagcaaa gcgagcttga acttgtcttc gcatggagca    2640
gtcatttctc agaaattagc aaccattatg catgtttctg ttggagatgc ctttgagctg    2700
aaatccgacg aaggaaaacg ctataaaatc aaagtttctg gtatcactga atgtacgca     2760 gggcatttta tatttatgaa tcaggactat tatcaaacgg tatttgctcg taagttccaa    2820
gaaaatgctt atctgataaa attgaaagat tcctctagca aaaatgtgca ggataccgca    2880
gcagccttca tgaaattaac tggtgtgcga gcagtcgtac aaaatacagg cattttggaa    2940
caaattgatg tcattgtcaa atctcttggc tttgtaatgc agattttaac ctttgcctct    3000
attttactag ccattgtgat tctttataac ttgatgaata tcaatgttgc agagcggatt    3060
cgagaattat caacgattaa agtattggga tttcataata agaagtcac gctttatatt      3120 tatcgagaga ccattctttt gtctgttatt ggtattatcg taggcttgtt tttggggaat    3180
atcttacatc gctccctttt agagacgatt gctccagatg cctttcttct caatccgacc    3240
gtatcggtgt ttgtatatct tgtgccagtc ttttctatca tcatgatttt gattgtctta    3300
ggctttatgg tcaatgcaat attgagacgc attgacatgt tagaagcatt aaagtcggta    3360
gattgataa                                                            3369
```

<210> SEQ ID NO 2
<211> LENGTH: 1121
<212> TYPE: PRT
<213> ORGANISM: Streptococcus anginosus

<400> SEQUENCE: 2

```
Met Lys Lys Ser Ile Leu Asn Lys Asp Ile Trp Leu Ser Phe Arg Gln
1               5                   10                  15

Ser Lys Gly Arg Phe Leu Ser Ile Met Phe Leu Met Met Leu Gly Ser
            20                  25                  30

Phe Ala Leu Val Gly Leu Lys Ala Ala Ser Pro Asp Ile Glu Asn Ser
        35                  40                  45

Ala Asn Arg Tyr Leu Ser Gln Met Lys Met Met Asp Leu Ala Val Met
    50                  55                  60

Ser Asp Tyr Gly Ile Ser Lys Ala Asp Gln Lys Glu Leu Asn Ala Val
65                  70                  75                  80

Pro Asn Ala Gln Val Glu Tyr Gly Tyr Phe Thr Asp Thr Val Ile Gly
                85                  90                  95

Asp Ser Ser Thr Ser Val Arg Val Phe Ser Gln Thr Thr Asn Ile Ser
            100                 105                 110

Lys Phe Lys Leu Val Ser Gly His Phe Pro Ser Lys Glu Asn Gln Val
        115                 120                 125

Val Leu Ala Ser Phe Tyr Gln Gly Lys Tyr Lys Ile Gly Asp Ser Ile
    130                 135                 140

Thr Leu Asn Glu Glu Gly Thr Asn Asp Tyr Ala Leu Lys Gln His Thr
145                 150                 155                 160

Phe Thr Val Thr Gly Phe Val Asn Ser Glu Leu Ala Ser Thr Ile
                165                 170                 175

Ser Leu Gly Asn Ser Asn Ser Gly Ser Gly Thr Leu Ser Ala Tyr Ala
            180                 185                 190

Val Val Met Pro Lys Thr Phe Gln Ser Ser Val Tyr Thr Val Ala Arg
        195                 200                 205
```

```
Leu Lys Tyr Asp Asp Leu Lys Thr Leu Asn Ser Phe Gly Asp Ser Tyr
    210                 215                 220
Arg Lys Lys Val Lys Arg Tyr Glu Asn Glu Leu Glu Lys Leu Val Ala
225                 230                 235                 240
Asp Asn Gly Lys Asn Arg Leu Ser Glu Ile Lys Lys Gln Ala Gln Thr
                245                 250                 255
Lys Ile Ala Asp Gly Glu Ala Lys Ile Gln Thr Ser Gln Gln Ala Leu
            260                 265                 270
Ala Asp Ala Gln Gln Leu Arg Asn Ala Gln Asp Gln Ile Asp Gln
        275                 280                 285
Lys Arg Ala Asp Leu Glu Ala Ala Gln Gly Gln Ile Thr Glu Lys Glu
290                 295                 300
Ser Leu Leu Ala Gln Gly Ala Thr Gln Ile Ala Gln Ala Glu Gln Thr
305                 310                 315                 320
Leu Glu Asn Thr Lys Glu Lys Leu Asp Thr Ala Ala Ala Gln Leu Ser
                325                 330                 335
Ser Gly Trp Ala Gln Leu Asn Gln Thr Lys Thr Gln Leu Asp Gln Ala
            340                 345                 350
Ala Ser Gln Leu Ser Ala Ala Lys Glu Asn Val Thr Asn Ala Gln Ala
        355                 360                 365
Thr Leu Ala Thr Ala Gln Ala Glu Leu Glu Lys Gly Gln Val Gln Leu
370                 375                 380
Ala Ala Ala Lys Val Asp Leu Gln Lys Lys Met Thr Ala Leu Gln Ala
385                 390                 395                 400
Gln Gly Ile Asp Ser Ala Thr Val Pro Glu Ile Val Ala Ala Gln Thr
                405                 410                 415
Gln Leu Ala Gln Glu Glu Ala Lys Leu Asn Leu Val Arg Thr Glu Leu
            420                 425                 430
Glu Lys Lys Gln Ala Glu Phe Gln Thr Gly Leu Ser Gln Tyr Lys Ser
        435                 440                 445
Gln Glu Ala Leu Tyr Gln Ala Gly Leu Ala Gln Tyr Gln Ser Ala Ala
450                 455                 460
Glu Thr Leu Asn Ala Lys Gln Ala Glu Tyr Asp Ala Gly Leu Ala Gln
465                 470                 475                 480
Tyr Gln Ser Gly Gln Ala Thr Leu Arg Asn Lys Gln Ala Glu Tyr Gln
                485                 490                 495
Ala Gly Gln Ala Gln Leu Ala Gln Ala Lys Gln Gln Ile Ala Asp Gly
            500                 505                 510
Gln Ala Gln Leu Asp Gln Ala Gln Ala Thr Leu Asn Asp Lys Lys Thr
        515                 520                 525
Glu Tyr Glu Lys Gln Lys Lys Asp Ala Glu Thr Lys Ile Lys Asn Gly
530                 535                 540
Gln Ala Asp Ile Gln Lys Ala Lys Glu Glu Val Ala Gly Leu Ser Val
545                 550                 555                 560
Pro Thr Tyr Arg Val Tyr Thr Arg Arg Thr Phe Pro Gly Ala Asp Glu
                565                 570                 575
Tyr Thr Thr Thr Gly Asn Arg Ala Tyr Gly Ile Ser Ala Val Gly Asn
            580                 585                 590
Ala Phe Pro Ile Val Leu Tyr Leu Val Ala Ala Leu Val Thr Val Thr
        595                 600                 605
Thr Met Thr Arg Phe Val Ser Glu Glu Arg Thr Asn Ala Gly Val Leu
610                 615                 620
Lys Ala Leu Gly Tyr Arg Asn Gln Asp Val Val Lys Lys Phe Val Val
625                 630                 635                 640
```

```
Tyr Gly Leu Val Ser Ser Leu Leu Gly Thr Val Met Gly Ser Leu Leu
                645                 650                 655
Gly Thr Tyr Phe Leu Pro Tyr Ile Leu Gly Lys Thr Ile Phe Lys Thr
            660                 665                 670
Ser Thr Tyr Pro Asp Leu Arg Leu Glu Phe Tyr Trp Glu Ile Ser Leu
            675                 680                 685
Ile Ala Leu Leu Cys Ser Val Leu Cys Gly Val Ala Pro Ala Leu Tyr
        690                 695                 700
Ile Ala His Lys Glu Leu Lys Glu Lys Pro Ser Gln Leu Leu Leu Pro
705                 710                 715                 720
Lys Ala Pro Thr Lys Gly Ser Lys Ile Leu Leu Glu Arg Ile Asp Phe
                725                 730                 735
Ile Trp Arg Arg Leu Ser Phe Ala Gln Lys Val Thr Ala Arg Asn Ile
                740                 745                 750
Phe Arg Tyr Lys Gln Arg Met Leu Met Thr Ile Phe Gly Val Ala Gly
            755                 760                 765
Ser Val Ala Leu Leu Phe Ala Gly Leu Gly Met Ser Ser Ser Met Glu
        770                 775                 780
Gly Met Gly Asn Arg Gln Tyr Gly Glu Ile Ile Lys Tyr Asp Ala Val
785                 790                 795                 800
Ile Ser Gln Lys Gln His Leu Lys Ser Asp Glu Gln Ala Ala Ile Asn
                805                 810                 815
His Leu Leu Ala Asp Lys Lys Ile Ala Lys Lys His Gly Ile Tyr Gln
            820                 825                 830
Glu Thr Phe Thr Lys Lys Ile Lys Gly Ala Lys Asp Glu Gln Ser Leu
        835                 840                 845
Ala Leu Phe Val Thr Thr Gly Lys Asp Phe Tyr His Phe Ile Glu Leu
    850                 855                 860
Tyr Asp Ser Gln Ser Lys Ala Ser Leu Asn Leu Ser Ser His Gly Ala
865                 870                 875                 880
Val Ile Ser Gln Lys Leu Ala Thr Ile Met His Val Ser Val Gly Asp
                885                 890                 895
Ala Phe Glu Leu Lys Ser Asp Glu Gly Lys Arg Tyr Lys Ile Lys Val
            900                 905                 910
Ser Gly Ile Thr Glu Met Tyr Ala Gly His Phe Ile Phe Met Asn Gln
        915                 920                 925
Asp Tyr Tyr Gln Thr Val Phe Ala Arg Lys Phe Gln Glu Asn Ala Tyr
    930                 935                 940
Leu Ile Lys Leu Lys Asp Ser Ser Lys Asn Val Gln Asp Thr Ala
945                 950                 955                 960
Ala Ala Phe Met Lys Leu Thr Gly Val Arg Ala Val Gln Asn Thr
                965                 970                 975
Gly Ile Leu Glu Gln Ile Asp Val Ile Val Lys Ser Leu Gly Phe Val
            980                 985                 990
Met Gln Ile Leu Thr Phe Ala Ser Ile Leu Leu Ala Ile Val Ile Leu
        995                1000                1005
Tyr Asn Leu Met Asn Ile Asn Val Ala Glu Arg Ile Arg Glu Leu
    1010                1015                1020
Ser Thr Ile Lys Val Leu Gly Phe His Asn Lys Glu Val Thr Leu
    1025                1030                1035
Tyr Ile Tyr Arg Glu Thr Ile Leu Leu Ser Val Ile Gly Ile Ile
    1040                1045                1050
Val Gly Leu Phe Leu Gly Asn Ile Leu His Arg Ser Leu Leu Glu
```

| | | | | | | | | | 1055 | | | 1060 | | | 1065 | |

Thr Ile Ala Pro Asp Ala Phe Leu Leu Asn Pro Thr Val Ser Val
     1070            1075                1080

Phe Val Tyr Leu Val Pro Val Phe Ser Ile Ile Met Ile Leu Ile
 1085                1090                1095

Val Leu Gly Phe Met Val Asn Ala Ile Leu Arg Arg Ile Asp Met
 1100                1105                1110

Leu Glu Ala Leu Lys Ser Val Asp
     1115            1120

<210> SEQ ID NO 3
<211> LENGTH: 30
<212> TYPE: DNA
<213> ORGANISM: Artificial
<220> FEATURE:
<223> OTHER INFORMATION: Primer

<400> SEQUENCE: 3
atgaaaaaat ccattctaaa taaggatatc                              30

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
aagactggca caagatatac                                         20

<210> SEQ ID NO 5
<211> LENGTH: 27
<212> TYPE: DNA
<213> ORGANISM: Artificial
<220> FEATURE:
<223> OTHER INFORMATION: Primer

<400> SEQUENCE: 5
gcggatccgg tcattttcca agcaagg                                 27

<210> SEQ ID NO 6
<211> LENGTH: 36
<212> TYPE: DNA
<213> ORGANISM: Artificial
<220> FEATURE:
<223> OTHER INFORMATION: Primer

<400> SEQUENCE: 6
gctgtcgact tattaaattc agcctgcttt ttctcc                       36

<210> SEQ ID NO 7
<211> LENGTH: 18
<212> TYPE: DNA
<213> ORGANISM: Artificial
<220> FEATURE:
<223> OTHER INFORMATION: Primer

<400> SEQUENCE: 7
agagtttgat cctggctc                                           18

<210> SEQ ID NO 8
<211> LENGTH: 19
<212> TYPE: DNA
<213> ORGANISM: Artificial
<220> FEATURE:

<223> OTHER INFORMATION: Primer

<400> SEQUENCE: 8
ggttaccttg ttacgactt                                               19

<210> SEQ ID NO 9
<211> LENGTH: 27
<212> TYPE: DNA
<213> ORGANISM: Artificial
<220> FEATURE:
<223> OTHER INFORMATION: Primer

<400> SEQUENCE: 9
caatttcaca caggaaacag ctatgac                                      27

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10
gtaaaacgac ggccagtgaa ttg                                          23

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
caaggaattg attcagcaac agtgc                                        25

<210> SEQ ID NO 12
<211> LENGTH: 25
<212> TYPE: DNA
<213> ORGANISM: Artificial
<220> FEATURE:
<223> OTHER INFORMATION: Primer

<400> SEQUENCE: 12
cttctcaaca agcattggca gatgc                                        25

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
gtgtgtatac acgtcggaca tttcc                                        25

<210> SEQ ID NO 14
<211> LENGTH: 26
<212> TYPE: DNA
<213> ORGANISM: Artificial
<220> FEATURE:
<223> OTHER INFORMATION: Primer

<400> SEQUENCE: 14
ggtacagtaa tgggaagttt gttagg                                       26

<210> SEQ ID NO 15

-continued

<211> LENGTH: 24
<212> TYPE: DNA
<213> ORGANISM: Artificial
<220> FEATURE:
<223> OTHER INFORMATION: Primer

<400> SEQUENCE: 15
gcggattgac ttcatttggc gtcg                                          24

<210> SEQ ID NO 16
<211> LENGTH: 25
<212> TYPE: DNA
<213> ORGANISM: Artificial
<220> FEATURE:
<223> OTHER INFORMATION: Primer

<400> SEQUENCE: 16
ggtttgggga tgtcttcttc catgg                                         25

<210> SEQ ID NO 17
<211> LENGTH: 24
<212> TYPE: DNA
<213> ORGANISM: Artificial
<220> FEATURE:
<223> OTHER INFORMATION: Primer

<400> SEQUENCE: 17
gcatctcaaa tcagacgagc aagc                                          24

<210> SEQ ID NO 18
<211> LENGTH: 24
<212> TYPE: DNA
<213> ORGANISM: Artificial
<220> FEATURE:
<223> OTHER INFORMATION: Primer

<400> SEQUENCE: 18
cttgaacttg tcttcgcatg gagc                                          24

<210> SEQ ID NO 19
<211> LENGTH: 26
<212> TYPE: DNA
<213> ORGANISM: Artificial
<220> FEATURE:
<223> OTHER INFORMATION: Primer

<400> SEQUENCE: 19
gactattatc aaacggtatt tgctcg                                        26

<210> SEQ ID NO 20
<211> LENGTH: 25
<212> TYPE: DNA
<213> ORGANISM: Artificial
<220> FEATURE:
<223> OTHER INFORMATION: Primer

<400> SEQUENCE: 20
ccaattcact tgaattgacg aatcc                                         25

<210> SEQ ID NO 21
<211> LENGTH: 23
<212> TYPE: DNA
<213> ORGANISM: Artificial
<220> FEATURE:
<223> OTHER INFORMATION: Primer#

<400> SEQUENCE: 21

```
gcccaacctg aagacagttg agc                                         23

<210> SEQ ID NO 22
<211> LENGTH: 25
<212> TYPE: DNA
<213> ORGANISM: Artificial
<220> FEATURE:
<223> OTHER INFORMATION: Primer

<400> SEQUENCE: 22
ctgacgaaaa gagagccaga tatcc                                       25

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23
ctgataccat aatctgacat cactgc                                      26

<210> SEQ ID NO 24
<211> LENGTH: 25
<212> TYPE: DNA
<213> ORGANISM: Artificial
<220> FEATURE:
<223> OTHER INFORMATION: Primer

<400> SEQUENCE: 24
gaagttgaac tatctccaat caccg                                       25

<210> SEQ ID NO 25
<211> LENGTH: 19
<212> TYPE: DNA
<213> ORGANISM: Artificial
<220> FEATURE:
<223> OTHER INFORMATION: Primer

<400> SEQUENCE: 25
tattcgctta gaaaattaa                                              19

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
gcaagttctt cagcttgttt                                             20

<210> SEQ ID NO 27
<211> LENGTH: 37
<212> TYPE: DNA
<213> ORGANISM: Artificial
<220> FEATURE:
<223> OTHER INFORMATION: Primer

<400> SEQUENCE: 27
gctgtcgact tattaagcac gattccccgt tgttgtg                          37
```

MARKER OF *STREPTOCOCCUS ANGINOSUS/ STREPTOCOCCUS CONSTELLATUS* (MOAC) AND USES THEREOF

CROSS REFERENCE TO A RELATED APPLICATION

This application is a National Stage Application of International Application Number PCT/EP2009/004416, filed Jun. 18, 2009; which claims priority to European Application No. 08011200.6, filed Jun. 19, 2008; which are incorporated herein by reference in their entirety.

The present invention relates to nucleic acids, vectors and polypeptides that are suitable markers for detecting *Streptococcus* strains of the *anginosus* group, preferably for detecting *Streptococcus anginosus* and/or *Streptococcus constellatus* as well as for discriminating *Streptococcus anginosus* and/or *Streptococcus constellatus* from other streptococci. The present invention furthermore relates to these nucleic acids and polypeptides for use in the diagnosis and/or prognosis of infections with *Streptococcus* strains of the *anginosus* group. The present invention furthermore relates to methods utilizing these nucleic acids and polypeptides as well as to arrays and antibodies.

BACKGROUND OF THE INVENTION

Despite the availability of antibiotic treatment streptococcal infections remain a serious threat to human health. Within the genus "*Streptococcus*", that comprises a rather heterogeneous variety of species, are pathogens like *S. pyogenes*, *S. agalactiae*, and *S. pneumoniae* that have an prominent role in human infections. *S. pyogenes* is a major cause for pharyngitis and causes galling skin diseases. This streptococcal species is characterized by β-hemolysis and the presence of Lancefield group A carbohydrates on its surface. In recent years it has become clear, both from epidemiologic as well as from functional studies, that β-hemolytic streptococcal species, which belong to Lancefield group C and G, have a pathogenic potential which is similar to that of *S. pyogenes*. Like infections with *S. pyogenes*, infections with group C- and group G streptococci (GCS, GGS, or together GCGS) can develop into life threatening necrotizing fasciitis, sepsis, and streptococcal toxic shock syndrome. Not only acute stages of *S. pyogenes*- and GCGS infections are threatening to the patient's life. Auto-immune sequelae with an often fatal outcome, namely poststreptococcal glomerulonephritis and acute rheumatic fever (ARF), arise in the wake of streptococcal infections.

Lancefield groups C and G comprise a number of different species of which *S. dysgalactiae equisimilis* is considered as the most frequent in human infections. Other rather neglected species that can expose group C and G carbohydrates are those gathered under the umbrella-term "*anginosus* group". Their role in human infection is documented, but their epidemiological significance has not been sufficiently investigated and assessed. Streptococci of the *anginosus* group (*S. anginosus*, *S. constellatus*, *S. intermedius*), which were formerly also referred to as *S. milleri*, are associated with purulent infections and severe abscess formation in the deep neck, the central nervous system and in inner organs. They exhibit a prominent phenotypic as well as immunogenic diversity as compared to other streptococci. Although the majority of isolates is non-β-hemolytic, there are β-hemolytic strains of each of the three species. When they carry a typable Lancefield group antigen, it belongs to group F, C, A, or G (for details see: (1)). Moreover, data base entries indicate that strains of the *anginosus* group may carry M proteins.

Microbiological routine diagnostic of streptococcal infections is often restricted to determination of the type of hemolysis and of the Lancefield group. Identification to the species level is rarely carried out and under these conditions bares a considerable risk for misidentification of causative pathogens. Consequently our insight into the epidemiology of infections with β-hemolytic streptococci is not precise. Comprehensive insight, however, is necessary for the development of improved treatments, aspired vaccination programs (although primarily targeting *S. pyogenes*), and the survey of the latter.

Thus, the present invention aims to provide means and methods for the detection of *Streptococcus* strains of the *anginosus* group, in particular of *Streptococcus anginosus* and/or *Streptococcus constellatus*, which allow a reliable identification and, thus, diagnosis and/or prognosis of respective infections.

SUMMARY OF THE INVENTION

According to the present invention this object is solved by providing nucleic acids that comprise the nucleotide sequence of moac or fragments thereof or that comprise the nucleotide sequence encoding the respective moac protein or its fragments, wherein the gene designation moac refers to marker of *S. anginosus* and *S. constellatus*.

Preferably, a nucleic acid of the present invention is selected from the group of:
(a) a nucleic acid comprising the nucleotide sequence of SEQ ID NO. 1,
(b) a nucleic acid comprising a nucleotide sequence which is at least 70% identical, preferably at least 80% identical to the nucleotide sequence of SEQ ID NO. 1,
(c) a nucleic acid comprising a fragment of at least 500, preferably at least 700 contiguous nucleotides of SEQ ID NO. 1,
(d) a nucleic acid encoding a polypeptide comprising the amino acid sequence of SEQ ID NO. 2,
(e) a nucleic acid encoding a polypeptide, which is at least 70% identical, preferably at least 80% identical or identical to the amino acid sequence of SEQ ID NO. 2,
(f) a nucleic acid encoding a polypeptide, comprising a fragment of at least 100, 200 or 300 contiguous amino acids of SEQ ID NO. 2,
(g) a nucleic acid comprising a fragment of 60 to 100, preferably 70, contiguous nucleotides of SEQ ID NO. 1,
(h) a nucleic acid the complementary strand of which hybridizes, preferably under stringent conditions, to a polynucleotide as defined in any one of (a) to (g), or the complementary strand of such a nucleic acid.

According to the present invention this object is furthermore solved by providing vectors comprising the nucleic acid of the invention.

According to the present invention this object is furthermore solved by providing moac polypeptides.

Preferably, a polypeptide of the present invention is selected from the group of:
(a) a polypeptide encoded by a nucleic acid comprising the nucleotide sequence of SEQ ID NO. 1,
(b) a polypeptide encoded by a nucleic acid comprising a nucleotide sequence which is at least 70% identical, preferably at least 80% identical to the nucleotide sequence of SEQ ID NO. 1, (c) a polypeptide encoded by a nucleic acid comprising a fragment of at least 500, preferably at least 700 contiguous nucleotides of SEQ ID NO. 1,
(d) a polypeptide comprising the amino acid sequence of SEQ ID NO. 2,
(e) a polypeptide, which is at least 70% identical, preferably at least 80% identical or identical to the amino acid sequence of SEQ ID NO. 2,
(f) a naturally occurring variant or a derivative of a polypeptide comprising the amino acid sequence of SEQ ID NO. 2 or of a polypeptide of any of (a) to (e),
(g) a fragment of the polypeptide of any of (a) to (f) comprising a fragment of at least 100, 200 or 300 contiguous amino acids of SEQ ID NO. 2.

According to the present invention this object is furthermore solved by providing cells comprising the nucleic acid(s), vector(s) or polypeptide(s) of the invention.

According to the present invention this object is furthermore solved by providing arrays comprising the nucleic acid(s) or polypeptide(s) of the invention.

According to the present invention this object is furthermore solved by providing the nucleic acid(s) or polypeptide(s) of the invention for use in the diagnosis and/or prognosis of infections with *Streptococcus* strains of the *anginosus* group, preferably *Streptococcus anginosus* and *Streptococcus constellatus*, wherein the nucleic acid(s) or polypeptide(s) of the invention are preferably used as marker for detecting *Streptococcus anginosus* and/or *Streptococcus constellatus*. Preferably, said nucleic acid(s), vector(s) or polypeptide(s) of the invention are used for discriminating *Streptococcus anginosus* and/or *Streptococcus constellatus* from other members of the genus *Streptococcus*, like from other *Streptococcus* strains of the *anginosus* group, preferably from *Streptococcus intermedius*, from other oral streptococci, and from beta-hemolytic streptococci, preferably *Streptococcus pyogenes* and *Streptococcus dysgalactiae equisimilis*.

According to the present invention this object is furthermore solved by providing a method for detecting the presence of and/or identifying *Streptococcus* strains of the *anginosus* group, preferably of *Streptococcus anginosus* and/or *Streptococcus constellatus*, in a sample.

The method of the invention preferably comprises the following steps:
(a) providing a sample to be tested,
(b) optionally, extracting/isolating nucleic acid from said sample or lysing said sample,
(c) performing a nucleic acid amplification with at least one oligonucleotide derived from a nucleic acid of claim 1 or 2 as primer,
(d) detecting the presence of an amplification product of step (c), which is indicative of the presence of a nucleic acid of *Streptococcus anginosus* and/or *Streptococcus constellatus*, in the sample.

According to the present invention this object is furthermore solved by providing the use of the nucleic acid(s) or polypeptide(s) of the invention or of fragments of the polypeptide(s) for the development of a vaccine which is specific for *Streptococcus anginosus* and/or *Streptococcus constellatus*.

According to the present invention this object is furthermore solved by providing antibodies or antisera specific for *Streptococcus anginosus* and/or *Streptococcus constellatus*, wherein antibodies or antisera are specific for the polypeptide(s) of the invention.

According to the present invention this object is furthermore solved by providing a method for the species determination of *Streptococcus* strains of the *anginosus* group preferably for *Streptococcus anginosus* and/or *Streptococcus constellatus*, comprising the use of the antibodies or antisera of the invention.

According to the present invention this object is furthermore solved by providing a kit for diagnosis and/or prognosis of *Streptococcus* strains of the *anginosus* group, preferably for *Streptococcus anginosus* and/or *Streptococcus constellatus*.

A kit of the invention comprises preferably
oligonucleotides selected from SEQ ID NOs. 3 to 6, reagents and excipients for performing the detecting methods/uses of the invention,
and/or antibody or antiserum/antibodies or antisera of the invention, reagents and excipients for performing the species determination method of the invention,
and/or an array comprising nucleic acid(s) comprising a fragment of 60 to 100, preferably 70, contiguous nucleotides of SEQ ID NO. 1 or the complementary strand of such nucleic acid(s).

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Marker Gene and Protein Moac

As outlined above, the present invention provides nucleic acids that comprise the nucleotide sequence of moac or fragments thereof or that comprise the nucleotide sequence encoding the respective moac protein or its fragments.

The gene designation moac refers to marker of *Streptococcus anginosus* and *Streptococcus constellatus*.

The inventors discovered a new open reading frame/gene in a collection of oral streptococci, which consisted of 129 clinical isolates of which 29 belong to the *anginosus* group (17 *S. anginosus*, 9 *S. constellatus*, 4 *S. intermedius*). Eighty strains of the collection are members of the *mitis* group (*S. mitis*, *S. oxalis*, *S. sanguinis*, *S. parasanguinis*). Thirteen strains have been typed as *S. salivarius* and two as *S. bovis*. A specific PCR for the new ORF was performed and specific PCR products were obtained exclusively within the *anginosus* group. Negative moac-PCR segregates *S. intermedius* from the strains of the other two species *S. anginosus* and *S. constellatus* which were all tested positive. The results were confirmed in experiments with reference strains from the DSMZ (Deutsche Sammlung für Mikroorganismen and Zellkulturen), for details see Examples and Figures. The results demonstrate that the newly discovered gene is a marker that discriminates *S. anginosus* and *S. constellatus* from other (oral) streptococci. The gene was therefore designated moac (marker of *S. anginosus* and *S. constellatus*).

The inventors performed inverted PCR experiments on *S. anginosus* strain SV52 and identified an open reading frame (ORF) of 3363 bp that codes for a 124 kDa protein.

The nucleotide sequence of that ORF is shown in SEQ ID NO. 1, the respective amino acid sequence is shown in SEQ ID NO. 2.

In an embodiment, a nucleic acid of the invention comprises the nucleotide sequence of SEQ ID NO. 1 or a nucleotide sequence, which is at least 70% identical, preferably at least 80% identical, more preferably at least 90% identical, even more preferably at least 95% identical, most preferably at least 99% identical to the nucleotide sequence of SEQ ID NO. 1.

In an embodiment, a nucleic acid of the invention encodes a polypeptide comprising the amino acid sequence of SEQ ID NO. 2 or a polypeptide, which is at least 70% identical, preferably at least 80% identical, more preferably at least 90% identical, even more preferably at least 95% identical, most preferably at least 99% identical or identical to the amino acid sequence of SEQ ID NO. 2.

In an embodiment, a nucleic acid of the invention comprises a fragment of SEQ ID NO. 1. Preferred fragments are at least 500, preferably at least 700 contiguous nucleotides of SEQ ID NO. 1.

In other embodiments of the invention, preferred fragments are 60 to 100, preferably 70, contiguous nucleotides of SEQ ID NO. 1. These nucleic acids are preferably suitable for the development of arrays, such as microarrays.

In an embodiment, a nucleic acid of the invention encodes a polypeptide, comprising a fragment of SEQ ID NO. 2, preferably a fragment of at least 100, 200 or 300 contiguous amino acids of SEQ ID NO. 2.

Preferably, the complementary strand of a nucleic acid of the invention hybridizes, preferably under stringent conditions, to a polynucleotide as defined above. In the context of the present specification, the term "stringent hybridization conditions" or "stringent conditions" refers to conditions under which a nucleic acid hybridizes to form a stable complex (e.g. a duplex) with its complement, but to a minimal number of other sequences. The stability of the complex is a function of salt concentration and temperature (See, for example, Sambrook et al., Molecular Cloning: A Laboratory Manual 2d Ed. (Cold Spring Harbor Laboratory, (1989)). Stringency levels used to hybridize nucleic acids can be readily varied by those of skill in the art. A preferred example of stringent hybridization conditions includes hybridization in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll) at a temperature of about 45° C. for a period of several hours. The hybridization solution is then removed, and non-specifically bound nucleic acid is removed by repeated washing with 1×SSC at increasing temperatures (up to 65° C.).

Thus, a nucleic acid of the present invention is preferably selected from the group of:
(a) a nucleic acid comprising the nucleotide sequence of SEQ ID NO. 1,
(b) a nucleic acid comprising a nucleotide sequence, which is at least 70% identical, preferably at least 80% identical, more preferably at least 90% identical, even more preferably at least 95% identical, most preferably at least 99% identical to the nucleotide sequence of SEQ ID NO. 1,
(c) a nucleic acid comprising a fragment of at least 500, preferably at least 700 contiguous nucleotides of SEQ ID NO. 1,
(d) a nucleic acid encoding a polypeptide comprising the amino acid sequence of SEQ ID NO. 2,
(e) a nucleic acid encoding a polypeptide, which is at least 70% identical, preferably at least 80% identical, more preferably at least 90% identical, even more preferably at least 95% identical, most preferably at least 99% identical or identical to the amino acid sequence of SEQ ID NO. 2,
(f) a nucleic acid encoding a polypeptide, comprising a fragment of at least 100, 200 or 300 contiguous amino acids of SEQ ID NO. 2,
(g) a nucleic acid comprising a fragment of 60 to 100, preferably 70, contiguous nucleotides of SEQ ID NO. 1,
(h) a nucleic acid the complementary strand of which hybridizes, preferably under stringent conditions, to a polynucleotide as defined in any one of (a) to (g),
or the complementary strand of such a nucleic acid.

A nucleic acid of the present invention comprises DNA, RNA, PNA, CNA, or other modified nucleotides, or combinations thereof.

As outlined above, the present invention provides a vector or vectors that comprise the nucleic acid(s) of the present invention.

Preferably, the nucleic acid(s) of the present invention is/are operatively linked to expression control sequences allowing expression in cells.

Such vectors are known in the art, such that the skilled artisan is able to design and/or choose the respective vector(s) which are suitable for a respective application.

As outlined above, the present invention provides moac polypeptide(s) or protein(s).

The inventors performed inverted PCR experiments on *S. anginosus* strain SV52 and identified an open reading frame (ORF) of 3363 bp (see SEQ ID NO. 1) that codes for a 124 kDa protein (see SEQ ID NO. 2). Transcription of the gene was detectable (see FIG. 1C). Computational analysis predicts a membrane protein with seven transmembrane regions and a signal peptide for extracellular secretion (see FIG. 1B). The predicted protein further consists of two larger extracellular regions, one of 23 kDa between the 4th and the 5th transmembrane region and an extracellular N-terminal of 60 kDa. Interestingly, the central part of the N-terminal extracellular region contains a stretch of heptad-repeats, which may allow coiled-coil oligomerization. Prediction of seven transmembrane regions suggests a receptor function or a function in transport processes.

A polypeptide or protein of the present invention is selected from the group of:
(a) a polypeptide encoded by a nucleic acid comprising the nucleotide sequence of SEQ ID NO. 1,
(b) a polypeptide encoded by a nucleic acid comprising a nucleotide sequence, which is at least 70% identical, preferably at least 80% identical, more preferably at least 90% identical, even more preferably at least 95% identical, most preferably at least 99% identical to the nucleotide sequence of SEQ ID NO. 1,
(c) a polypeptide encoded by a nucleic acid comprising a fragment of at least 500, preferably at least 700 contiguous nucleotides of SEQ ID NO. 1,
(d) a polypeptide comprising the amino acid sequence of SEQ ID NO. 2,
(e) a polypeptide, which is at least 70% identical, preferably at least 80% identical, more preferably at least 90% identical, even more preferably at least 95% identical, most preferably at least 99% identical or identical to the amino acid sequence of SEQ ID NO. 2,
(f) a naturally occurring variant or a derivative of a polypeptide comprising the amino acid sequence of SEQ ID NO. 2 or of a polypeptide of any of (a) to (e),
(g) a fragment of the polypeptide of any of (a) to (f) comprising a fragment of at least 100, 200 or 300 contiguous amino acids of SEQ ID NO. 2.

Preferably, the polypeptide(s)/protein(s) of the invention is encoded by nucleic acid(s) of the invention, as described and defined herein.

In an embodiment of the invention, fragments of the polypeptide(s) of the invention are used for generating antibodies or antisera or vaccines. Such fragments/peptides are fragments according to (c) or (g) above, but shorter fragments (such 10 to 100, preferably 25 to 75 contiguous amino acids of SEQ ID NO. 2) or longer fragments are also suitable depending on the method that is used for generating antibodies or antisera or vaccines. The skilled artisan will be able to choose the suitable fragment size.

Preferably, the polypeptide(s) of the invention are derived from Streptococcus strains of the anginosus group, preferably from Streptococcus anginosus.

Streptococci of the "anginosus group" or Streptococcus strains of the "anginosus group" are S. anginosus, S. constellatus, S. intermedius and were formerly also referred to as S. milleri. They are associated with purulent infections and severe abscess formation in the deep neck, the central nervous system and in inner organs. They exhibit a prominent phenotypic as well as immunogenic diversity as compared to other streptococci. Although the majority of isolates is non-β-hemolytic, there are β-hemolytic strains of each of the three species. When they carry a typable Lancefield group antigen, it belongs to group F, C, A, or G (for details see: (1)).

As outlined above, the present invention provides cell(s) that contain the nucleic acid(s), the vector(s) or the polypeptide(s) of the invention.

Suitable cells and cell lines are known in the art. A suitable cell is e.g. able to express the polypeptide(s) of the invention. Cells of the invention are preferably eukaryotic or prokaryotic cells.

As outlined above, the present invention provides array(s) that comprise the nucleic acid(s) or the polypeptide(s) of the invention.

"Arrays" or "microarrays" are known in the art and comprise e.g. DNA microarrays, antibody microarrays, tissue microarrays, protein microarrays. They are used e.g. for gene expression analysis or profiling, for measuring changes in expression levels, for detecting single nucleotide polymorphisms, for detecting proteins from cell lysate solutions/samples, for detecting nucleic acids from cell lysate solutions/samples etc. In the present invention, the arrays are preferably suitable for detecting nucleic acids and/or proteins in samples.

Preferably, the arrays of the invention comprise fragments of the nucleic acid(s) or the polypeptide(s) of the invention, wherein the fragments are defined herein or can be chosen by the skilled artisan.

Preferably, the arrays of the invention comprise nucleic acids comprising fragment(s) of 60 to 100, preferably 70, contiguous nucleotides of SEQ ID NO. 1, or the complementary strand of such a nucleic acids. The skilled artisan will be able to choose suitable fragment sizes and sequences for generating arrays that are suitable for the respective application.

Preferably, the arrays of the invention comprise said fragments of the nucleic acid(s) which are labelled and/or which function as probes.

The arrays of the invention are in particular suitable for the methods and uses described herein. They can comprise further nucleic acid(s), protein(s) and fragments thereof etc. in order to detect further proteins/nucleic acids, e.g. for profiling/comparing/assessing whole organisms (like streptococci strains) or (biological) samples or bacterial strain collections.

Diagnosis Marker

As outlined above, the present invention provides the nucleic acid(s) or polypeptide(s) of the invention for use in the diagnosis and/or prognosis of infections with Streptococcus strains of the anginosus group, preferably Streptococcus anginosus and Streptococcus constellatus.

As discussed above, Streptococcus strains of the anginosus group, especially Streptococcus anginosus and Streptococcus constellatus, are associated with purulent infections and severe abscess formation in the deep neck and in inner organs.

Preferably, the nucleic acid(s) or polypeptide(s) of the invention are used as marker for detecting Streptococcus anginosus and/or Streptococcus constellatus.

Preferably, said nucleic acid(s) or polypeptide(s) of the invention are used for discriminating Streptococcus anginosus and/or Streptococcus constellatus from:
  other members of the genus Streptococcus
    preferably other Streptococcus strains of the anginosus group, preferably from Streptococcus intermedius,
  other oral streptococci,
  and beta-hemolytic streptococci,
    preferably Streptococcus pyogenes and Streptococcus dysgalactiae equisimilis.

Preferably, said use comprises a nucleic acid amplification, preferably a PCR, wherein the nucleic acid(s) of the invention are specifically amplified, when e.g. present in a sample, and then preferably detected.

As shown and discussed herein, in particular in the Examples and Table 1, the nucleic acid(s) or polypeptide(s) of the invention are a specific marker for Streptococcus anginosus and Streptococcus constellatus and which in particular discriminate(s) them from other streptococcal species (preferably from Streptococcus intermedius), from other oral streptococci and beta-hemolytic streptococci (preferably Streptococcus pyogenes and Streptococcus dysgalactiae equisimilis).

The nucleic acid(s) or polypeptide(s) of the invention can be utilized as markers in vivo as well as in vitro.

Methods Utilizing the Moac Marker Gene and/or Protein

As outlined above, the present invention provides methods for detecting the presence of Streptococcus strains of the anginosus group and/or for identifying Streptococcus strains of the anginosus group, preferably of Streptococcus anginosus and/or Streptococcus constellatus, in a sample.

In a step (a) of the method a sample to be tested is provided.
A sample is preferably selected from
  faeces,
  swabs of the oral cavity,
  bodiliy fluids,
    like saliva, pus, sputum, blood, and urine, or
  samples from infected or non-infected tissues (tissue samples),
    like skin or abscesses of different origin (peritonsillar, inner organs, heart valve and vegetations on the heart valve, etc.).

In a subsequent optional step (b) of the method said sample is lysed and/or nucleic acid is extracted and/or isolated from said sample.

Methods and procedures for the extraction/isolation of nucleic acids from samples as well as bacterial lysis methods and procedures are known in the art.

Preferably, the genomic DNA is isolated from the sample.

When the sample is lysed, the bacteria potentially contained in the sample are lysed, such that the respective bacterial lysates containing nucleic acid are then used further in the method.

In a subsequent step (c) of the method a nucleic acid amplification is performed.

The nucleic acid amplification is performed in the sample provided or in the sample that was treated in the optional step (b), such as genomic DNA or bacterial lysate of the sample.

Preferably, the nucleic acid amplification is selected from PCR, RT-PCR, real time PCR, multiplex PCR. Further nucleic acid amplification methods/procedures can be utilized.

The nucleic acid amplification is performed with at least one oligonucleotide that is derived from a nucleic acid of the invention, as described and defined above, as primer, preferably with at least one oligonucleotide derived from SEQ ID NO. 1. Preferably two or more oligonucleotides derived from SEQ ID NO. 1 are used as primers.

Preferably, at least one (preferably two) oligonucleotide is selected from SEQ ID NOs. 3 to 6 and used preferably as primer, preferably oligonucleotides with SEQ ID NOs. 3 and 4 and/or oligonucleotides with SEQ ID NOs. 5 and 6.

Preferably, primer pair of

```
                                              [SEQ ID NO. 3]
5'-ATG AAA AAA TCC ATT CTA AAT AAG GAT ATC-3'
and

[SEQ ID NO. 4]
5'-AGG ACT GGC ACA AGA TAT AC-3'.
```

Preferably, primer pair of

```
                                              [SEQ ID NO. 5]
5'-GCG GAT CCG GTC ATT TTC CAA GCA AGG-3'
and

[SEQ ID NO. 6]
5'-GCT GTC GAC TTA TTA AAT TCA GCC TGC TTT TTC
TCC-3'.
```

Further primer sequences can be derived from SEQ ID NO. 1.

In a subsequent step (d) the presence of an amplification product of step (c) is detected.

The presence of an amplification product of step (c) is indicative of the presence of a nucleic acid of *Streptococcus anginosus* and/or *Streptococcus constellatus* in the sample.

Thus, the absence of an amplification product of step (c) is indicative of the absence of a nucleic acid of *Streptococcus anginosus* and/or *Streptococcus constellatus* in the sample, but can be indicative for the presence of a nucleic acid of other *Streptococcus* strains of the *anginosus* group, in particular in combination with further detection tests.

Methods/procedures for detecting nucleic acid amplification products are known in the art, such as gel electrophoresis, blotting techniques, probes, labelled probes etc.

In a preferred embodiment oligonucleotide sequences can be derived from SEQ ID NO. 1 and utilized as probes.

A method for detecting the presence of and/or identifying *Streptococcus anginosus* and/or *Streptococcus constellatus*, in a sample according to the present invention comprises the following steps:
(a) providing a sample to be tested,
(b) optionally, extracting/isolating nucleic acid from said sample or lysing said sample,
(c) performing a nucleic acid amplification with at least one oligonucleotide derived from a nucleic acid of claim 1 or 2 as primer,
(d) detecting the presence of an amplification product of step (c), which is indicative of the presence of a nucleic acid of *Streptococcus anginosus* and/or *Streptococcus constellatus*, in the sample.

In a preferred embodiment, the method of the invention comprises the use of an array of the invention, wherein the array comprises the nucleic acid(s) of the invention or fragments thereof.

In a preferred embodiment, the method of the invention is utilized for discriminating *Streptococcus anginosus* and/or *Streptococcus constellatus* from:
other members of the genus *Streptococcus*
  preferably other *Streptococcus* strains of the *anginosus* group, preferably from *Streptococcus intermedius*,
other oral streptococci,
and beta-hemolytic streptococci,
  preferably *Streptococcus pyogenes* and *Streptococcus dysgalactiae equisimilis*.

In a preferred embodiment, the method of the invention is utilized for the diagnosis and/or prognosis of infections with *Streptococcus anginosus* and/or *Streptococcus constellatus*.

Vaccines, Antibodies and Kits

As outlined above, the present invention provides the use of the nucleic acid(s) or the polypeptide(s) of the invention or of fragments of the polypeptide(s) of the invention for the development of a vaccine which is specific for *Streptococcus anginosus* and/or *Streptococcus constellatus*.

Methods for developing and generating vaccines utilizing nucleic acids, polypeptides/proteins and fragments thereof are known in the art.

In an embodiment of the invention, fragments of the polypeptide(s) of the invention are used for generating antibodies or antisera or vaccines. Such fragments/peptides are fragments according to (c) or (g) as defined above, but shorter fragments (such 10 to 100, preferably 25 to 75 contiguous amino acids of SEQ ID NO. 2) or longer fragments are also suitable depending on the method that is used for generating antibodies or antisera or vaccines. The skilled artisan will be able to choose the suitable fragment size.

As outlined above, the present invention provides an antibody or antiserum which is specific for *Streptococcus anginosus* and/or *Streptococcus constellatus*.

Such an antibody or antiserum/antibodies or antisera is/are specific for the polypeptide(s) of the invention, as defined herein.

As outlined above, the present invention provides a method for the species determination of *Streptococcus* strains of the *anginosus* group, preferably for the species determination of *Streptococcus anginosus* and/or *Streptococcus constellatus*.

Such a species determination method comprises the use of the antibody or antiserum/antibodies or antisera of the invention.

As outlined above, the present invention provides kits for the diagnosis and/or prognosis of *Streptococcus* strains of the *anginosus* group, preferably kits for the diagnosis and/or prognosis of *Streptococcus anginosus* and/or *Streptococcus constellatus*.

A kit of the present invention comprises preferably:
oligonucleotides selected from SEQ ID NOs. 3 to 6 and/or oligonucleotides derived from the nucleic acid(s) of the invention, preferably from SEQ ID NO. 1,
  wherein the oligonucleotides are preferably used as primers and/or probes,
reagents and excipients for performing the detecting methods/detecting uses of the invention, such as for the nucleic acid amplification,
and/or
antibody(antibodies) or antiserum(antisera) of the invention,
reagents and excipients for performing the species determination method, and/or an array comprising nucleic acid(s) comprising a fragment of 60 to 100, preferably 70, contiguous nucleotides of SEQ ID NO. 1 or the complementary strand of such nucleic acid(s).

The inventors provide a fast and reliable PCR-method to distinguish S. anginosus and S. constellatus from other members of the genus, which besides diagnostic, preventive and therapeutic actions allows to assess their epidemiologic role in GCGS infections.

The following drawings and examples illustrate the present invention without, however, limiting the same thereto.

BRIEF DESCRIPTION OF THE DRAWINGS

FIG. 1: Amplification, characterization, and transcription analysis of a newly discovered ORF of S. anginosus.

(A) Gel electrophoresis after emm-PCR on S. anginosus isolate SV52 (SV52) and S. pyogenes strain A60 (A60). The latter was used as a control that possesses an emm3-gene. The S. anginosus strain generated a weak 1.1 kb product, as compared to the 1.4 kb product of the S. pyogenes strain. Inverse PCR based on the 1.1 kb sequence of SV52 revealed an ORF of 3363 bp that codes for a predicted membrane protein that is schematically depicted in B. Its N-terminal signal peptide (S) is followed by a large extracellular region of 60 kDa (ECR1). Its C-terminal half comprises seven transmembrane helices (1 to 7) and another large extracellular region of 23 kDa situated between the 4th and the 5th transmembrane helix. (C) Transcription of the newly discovered gene was detectable with four different primer pairs (I to IV). PCR after reverse transcription amplified sections of the 5'-region (I and IV) as well as 3'-region of the gene (II and III) (C). Positions of the PCR-products relative to the full length sequence and their calculated length in by are given in B.

EXAMPLES

Materials and Methods

Bacterial strains, Lancefield Typing, Genomic DNA

Clinical isolates of GGS and GCS were collected at the Department of Clinical Microbiology, Christian Medical College Vellore, India. This geographic region has a high incidence of group C and G streptococcal infections and acute rheumatic fever. The collection comprises throat-, pus-, sputum- and urine-isolates as well as one blood isolate.

Clinical isolates of oral streptococci were collected at the Institute for Medical Microbiology and Epidemiology of Infectious Diseases, University of Leipzig, Germany. The isolates were recovered from blood cultures, wound swabs, aspirates of peritonsillar abscesses, several other abscesses, and catheter tips.

Bacterial strains were sub-cultured on Columbia agar with 5% sheep blood (Becton Dickinson). Single colonies were grown overnight (37° C., 5% $CO_2$) in Todd-Hewitt broth (Becton Dickinson) supplemented with 0.5% yeast extract (THY).

When required the Lancefield group was determined using a streptococcal grouping kit (Oxoid). Genomic DNA was isolated using the DNeasy Blood and Tissue Kit (Qiagen) according to the manufacture's instructions. Incubation with proteinase K was carried out at 70° C.

Sequencing of 16S rRNA Genes

For amplification of the 16S rRNA gene a PCR was performed with a pair of generic primers for Gram-positive bacteria recommended by Takahashi et al., 1997 (3):

```
                                        SEQ ID NO. 7
Primer A      5'-AGA GTT TGA TCC TGG CTC-3'

SEQ ID NO. 8
primer B      5'-GGT TAC CTT GTT ACG ACT T-3'
```

The obtained PCR products were analysed by agarose (1%) gel electrophoresis, purified using the Qiagen PCR purification kit, and subsequently sequenced using primer A.

All emm PCR

Genomic DNA of streptococcus isolates was tested by PCR for the presence of emm and emm-like genes using the primers 1 and 2:

```
                                        SEQ ID NO. 25
primer 1     5'-TAT TCG CTT AGA AAA TTA A-3'

SEQ ID NO. 26
primer 2     5'-GCA AGT TCT TCA GCT TGT TT-3'
```

Inverse PCR and Sequencing of Moac

All emm PCR on the genomic DNA of S. anginosus strain SV52 produced a 1.1 kb fragment of moac which was then cloned into the pCR®2.1-TOPO® vector using the TOPO TA Cloning® kit (Invitrogen) and subsequently sequenced using the following primers

```
                                        SEQ ID NO. 9
M13 rev   5'-CAA TTT CAC ACA GGA AAC AGC TAT GAC-3'

SEQ ID NO. 10
M13 fwd   5'-GTA AAA CGA CGG CCA GTG AAT TG-3'
```

Inverse PCR was used to amplify the genomic DNA segments flanking the 1.1 kb fragment of moac. One µg of genomic DNA was digested separately with one up to three of the following enzymes: AseI, AvrII, BamHI, BglII, BsaI, BseYI, EcoRI, HindIII, NdeI, NsiI, PstI, SacI, SalI, SpeI, XbaI, XhoI (New England Biolabs)—for 16 h under conditions recommended by the manufacturer. Digested genomic DNA was diluted both 100-fold and 10-fold, and self-ligated. One µl of ligation mixture was used as a template for PCR using

```
forward primers
                                        SEQ ID NO. 11
moac1     5'-CAA GGC ATT GAT TCA GCA ACA GTG C-3'

SEQ ID NO. 12
moac3     5'-CTT CTC AAC AAG CAT TGG CAG ATG C-3'

SEQ ID NO. 13
moac6     5'-GTG TGT ATA CAC GTC GGA CAT TTC C-3'

SEQ ID NO. 14
moac7     5'-GGT ACA GTA ATG GGA AGT TTG TTA GG-3'

SEQ ID NO. 15
moac8     5'-GCG GAT TGA CTT CAT TTG GCG TCG-3'

SEQ ID NO. 16
moac9     5'-GGT TTG GGG ATG TCT TCT TCC ATG G-3'

SEQ ID NO. 17
moac10    5'-GCA TCT CAA ATC AGA CGA GCA AGC-3'
```

-continued

```
                                              SEQ ID NO. 18
moac11   5'-CTT GAA CTT GTC TTC GCA TGG AGC-3'

SEQ ID NO. 19
moac12   5'-GAC TAT TAT CAA ACG GTA TTT GCT CG-3'
and reverse primers
                                              SEQ ID NO. 20
moac2    5'-CCT ATT CAC TTG AAT TGA CGA ATC C-3'

SEQ ID NO. 21
moac4    5'-GCC CAA CCT GAA GAC AGT TGA GC-3'

SEQ ID NO. 22
moac5    5'-CTG ACG AAA AGA GAG CCA GAT ATC C-3'

SEQ ID NO. 23
moac13   5'-CTG ATA CCA TAA TCT GAC ATC ACT GC-3'

SEQ ID NO. 24
moac14   5'-GAA GTT GAA CTA TCT CCA ATC ACC G-3'
```

The PCR mixture (20 µl) contained primers (0.5 pmol/µl each; MWG), dATP, dTTP, dGTP, dCTP (0.2 mM each; Fermentas), MgCl2 (2.5 mM; Qiagen), Taq DNA polymerase (1 U; Qiagen), and 2 µl of PCR 10× buffer (Qiagen). PCR amplification was performed in a thermocycler (Biometra) with an initial denaturation (4 min at 96° C.), followed by 30 cycles of denaturation (40 s at 94° C.), annealing (30 s at 56° C.), and extension (1 min 30 s up to 3 min, 72° C.). A final extension was carried out for 5 min at 72° C. The obtained PCR products were analysed by agarose (1%) gel electrophoresis, purified for sequencing, using the Qiagen Gel extraction kit.

Screening for Moac

The genomic DNA of all the clinical isolates were tested by PCR for the presence of the moac-gene. For this purpose two primer pairs were used to amplify a 3272-bp fragment and additionally a 962-bp internal fragment of moac.

The 3272-bp fragment was amplified with

```
moac-SP
                                              [SEQ ID NO. 3]
5'-ATG AAA AAA TCC ATT CTA AAT AAG GAT ATC-3'
and moac-TMH7
                                              [SEQ ID NO. 4]
5'-AAG ACT GGC ACA AGA TAT AC-3'
```

The 962-bp fragment was amplified with

```
MOAC-BamH1
                                              [SEQ ID NO. 5]
5'-GCG GAT CCG GTC ATT TTC CAA GCA AGG-3'
and
MOAC-Sal1
                                              [SEQ ID NO. 6]
5'-GCT GTC GAC TTA TTA AAT TCA GCC TGC TTT TTC
TCC-3'
```

After initial denaturation (4 min at 96° C.) 25 cycles of denaturation (40 s at 94° C.), annealing (30 s at 53° C.), and extension (1 min 30 s), were performed, with a final extension step for 5 min at 72° C. (962-bp fragment). For the 3272-bp fragment was amplified with 30 cycles using an annealing temperature of 50° C. and an extension time of 3 min 20 s. The obtained PCR products were analysed by agarose (1%) gel electrophoresis.

Transcription of Moac

Total RNA was extracted from log-phase culture of *S. anginosus* strain SV52 using the RiboPure™ Bacteria-Kit (Ambion), according to the manufacturer's instructions. RNA was reverse transcribed with SuperScript™ II Reverse Transcriptase (Invitrogen) under conditions recommended by the manufacturer. After cDNA synthesis and inactivation of the reverse transcriptase at 70° C. for 15 minutes the mixture was filled up with 40 µl nuclease-free water. The single-stranded cDNA was then subjected to PCR. The transcription of moac was examined using four different primer pairs to amplify the 962-bp internal fragment described above
   with primers of SEQ ID NOs. 5 and 6,
a 552-bp fragment
   with primers moac1 (SEQ ID NO. 11) and SalI-moac-ECR (SEQ ID NO. 27)
a 657-bp fragment
   with primers moac11 (SEQ ID NO. 18) and moac-TMH7 (SEQ ID NO. 4)
and a 858-bp fragment
   with primers moac10 (SEQ ID NO. 17) and moac-TMH7 (SEQ ID NO. 4).

```
primer Sal1-moac-ECR [SEQ ID NO. 27]:
5'-GCT GTC GAC TTA TTA AGC ACG ATT CCC CGT TGT TGT
G-3'
```

Results

Screening for M-proteins by emm-Specific PCR in Clinical Isolates of β-hemolytic GCS/GGS A collection of GCGS was isolated from patients with clinical infections admitted to the Christian Medical College in Vellore, India. This geographic region has a high incidence of group C and G streptococcal infections and acute rheumatic fever. The study was designed to be cross species, therefore no pre-selection criteria other than type of hemolysis and Lancefield-typing were applied. Because of the fundamental role of M-proteins in acute streptococcal infections as well as in the pathogenesis of acute rheumatic fever, the distribution emm-types was examined by means of the emm-typing procedure that is suggested by the Center for Disease Control and Prevention (CDC). The occurrence of 47 emm-types, of which eight had not been known previously, indicates a high serotype diversity in this region, which is similar to the one reported for *S. pyogenes* (2). It is of note that 21% (62 strains) of the 301 stains did not produce a PCR product and thus, were considered as not emm-typable. The nature of these strains was further investigated and described at a later stage in this study.

Screening of emm-like Genes in Clinical Isolates of Non- and α-hemolytic Strains of the *anginosus* Group A recent survey at the university hospital in Leipzig (Germany) revealed that a considerable part of severe infections with oral streptococci was caused by strains that belong to the *anginosus* group. Moreover, database entries report the presence of M proteins in strains of the *anginosus* group. To investigate whether M proteins were involved in the pathogenesis of these infections, a collection of 12 *anginosus* group strains was included in the screening for emm-genes described above. For all isolates the PCR failed to amplify a product similar to the ones obtained with the majority of GCGS strains or to a control reaction with an *S. pyogenes* strain. In the sample of some strains a weak band at the size of 1.1 kb was observed (FIG. 1A). Sequencing did not reveal considerable similarities with emm-genes. The lack of stop-codons in one frame, however, motivated further investigations on that PCR product.

Gene Transcription and Characteristics of a Newly Discovered Protein of S. anginosus Inverted PCR experiments on S. anginosus strain SV52 identified an open reading frame (ORF) of 3363 bp that codes for a 124 kDa protein. Transcription of the gene was detectable (FIG. 1C). Computational analysis predicts a membrane protein with seven transmembrane regions and a signal peptide for extracellular secretion (FIG. 1B). The predicted protein further consists of two larger extracellular regions, one of 23 kDa between the 4th and the 5th transmembrane region and an extracellular N-terminal of 60 kDa. Interestingly, the central part of the N-terminal extracellular region contains a stretch of heptad-repeats, which may allow coiled-coil oligomerization. Prediction of seven transmembrane regions suggests a receptor function or a function in transport processes.

The Newly Discovered ORF is a Marker that Discriminates S. anginosus and S. constellatus from Other Oral Streptococci The distribution of the newly discovered ORF in a collection of oral streptococci was examined by PCR with two different primer pairs, as described above. Both primer combinations gave identical results. The collection consists of 129 clinical isolates of which 29 belong to the anginosus group (17 S. anginosus, 9 S. constellatus, 4 S. intermedius). Eighty strains of the collection are members of the mitis group (S. mitis, S. oralis, S. sanguinis, S. parasanguinis). Thirteen strains have been typed as S. salivarius and two as S. bovis.

Specific PCR products were obtained exclusively within the anginosus group. Negative moac-PCR segregates S. intermedius from the strains of the other two species S. anginosus and S. constellatus which were all tested positive. The results were confirmed in experiments with reference strains from the DSMZ (Deutsche Sammlung fair Mikroorganismen and Zellkulturen) (Table 1). Taken together, the results demonstrate that the newly discovered gene is a marker that discriminates S. anginosus and S. constellatus from other oral streptococci. The gene was therefore designated moac (marker of S. anginosus and S. constellatus).

TABLE 1

Distribution of moac within a collection of oral *streptococci*

| species | | strains | moac-PCR |
|---|---|---|---|
| anginosus group | | 31 | |
| | S. anginosus | 17 | + |
| | S. constellatus | 10 | + |
| | S. intermedius | 4 | − |
| bovis group | | 2 | |
| | S. bovis | 2 | − |

TABLE 1-continued

Distribution of moac within a collection of oral *streptococci*

| species | | strains | moac-PCR |
|---|---|---|---|
| mitis group | | 69 | |
| | S. gordonii | 4 | − |
| | S. mitis/S. oralis | 12 | − |
| | S. mitis | 8 | − |
| | S. oralis | 21 | − |
| | S. parasanguinis | 17 | − |
| | S. sanguinis | 7 | − |
| salivarius group | | 11 | |
| | S. salivarius | 11 | − |
| reference strains (DSMZ) | | | |
| anginosus group | | 4 | |
| | S. anginosus | 1 | + |
| | S. constellatus pharyngis | 1 | + |
| | S. constellatus constellatus | 1 | + |
| | S. intermedius | 1 | − |
| mutans group | | 1 | |
| | S. mutans | 1 | − |

Moac is a marker for S. anginosus and S. constellatus within the β-hemolytic Streptococci The data obtained with the collection of oral streptococci suggested that moac could also be exploited as a marker for β-hemolytic strains of the anginosus group. Both, to test the quality of moac as a marker and to examine the species distribution within β-hemolytic clinical GCS and GGS isolates from Vellore, the collection was subjected to both, 16S rRNA gene sequence analysis and moac-specific PCR (moac-PCR). Based on their 16S rRNA gene sequence the majority of strains could be specified as S. dysgalactiae equisimilis (242 of 301 strains). All these strains were negative in moac-PCR and, except of three strains, were emm-typable. Interestingly, all the 59 remaining strains that were not emm-typable could be assigned to the species S. anginosus by 16S rRNA gene sequencing. All these strains were positive in the moac-PCR. The experiments revealed that moac-PCR is a reliable method for identification of anginosus strains in collections of β-hemolytic GCGS. They, moreover, demonstrate that S. anginosus constitute 20% of the collection of β-hemolytic isolates from clinical infections in Vellore, which indicates a considerable epidemiological role of these pathogens in the acute infections.

The features disclosed in the foregoing description, in the claims and/or in the accompanying drawings may, both separately and in any combination thereof, be material for realizing the invention in diverse forms thereof.

REFERENCES

1. R. Facklam, *Clin Microbiol Rev* 15, 613 (October, 2002).
2. J. J. Jose, K. N. Brahmadathan, *Indian J Med Microbiol* 24, 127 (April, 2006).
3. T. Takahashi et al., *J Vet Med Sci* 59, 775 (September, 1997).

The invention claimed is:

1. An isolated nucleic acid selected from the group consisting of:
   (a) a nucleic acid comprising the nucleotide sequence of SEQ ID NO. 1,
   (b) a nucleotide sequence which is at least 95% identical to the nucleotide sequence of SEQ ID NO. 1,
   (c) a nucleic acid encoding a polypeptide comprising the amino acid sequence of SEQ ID NO. 2, and
   (d) a nucleic acid encoding a polypeptide, which is at least 95% identical to the amino acid sequence of SEQ ID NO. 2,
   or the full complementary strand of such a nucleic acid.

2. The isolated nucleic acid of claim 1, comprising DNA, RNA, PNA, or CNA.

3. An isolated vector comprising the nucleic acid of claim 1 and wherein the nucleic acid is operatively linked to expression control sequences allowing expression in host cells.

4. An isolated cell containing the nucleic acid of claim 1.

5. An assay comprising nucleic acids of claim 1.

6. A method for detecting whether a sample contains either of *Streptococcus anginosus* or *Streptococcus constellatus* wherein the method comprises the steps of
   (a) providing a sample to be tested,
   (b) optionally, extracting/isolating nucleic acid from said sample or lysing said sample,
   (c) performing a nucleic acid amplification with two oligonucleotides obtained from a nucleic acid of claim 1 as primers, and
   (d) detecting the presence of an amplification product of step (c),
   wherein the presence of said amplification product is indicative of the presence of *Streptococcus anginosus* and/or *Streptococcus constellatus*, in the sample.

7. The method of claim 6 for discriminating *Streptococcus anginosus* and/or *Streptococcus constellatus* from other members of the genus *Streptococcus*.

8. The method of claim 6 for diagnosis and/or prognosis of infections with *Streptococcus anginosus* and/or *Streptococcus constellatus*.

9. The method, according to claim 6, wherein the sample is selected from feces, swabs of the oral cavity, saliva, pus, sputum, blood, and urine, or wherein the sample is from infected or non-infected tissues.

10. The method, according to claim 6, wherein the nucleic acid amplification is selected from PCR, RT-PCR, real time PCR, and multiplex PCR.

11. The method, according to claim 6, wherein the oligonucleotide is selected from SEQ ID NO:3 to SEQ ID NO:6.

12. A kit for diagnosis and/or prognosis of *Streptococcus* strains of the *anginosus* group comprising:
    at least two oligonucleotides selected from SEQ ID NOs. 3 to 6, and
    reagents and excipients for performing nucleic acid amplification.

* * * * *

UNITED STATES PATENT AND TRADEMARK OFFICE
CERTIFICATE OF CORRECTION

PATENT NO. : 8,530,224 B2
APPLICATION NO. : 12/995052
DATED : September 10, 2013
INVENTOR(S) : Gursharan S. Chhatwal et al.

It is certified that error appears in the above-identified patent and that said Letters Patent is hereby corrected as shown below:

In the Specification

Column 9,
Line 21, "5' – AGG ACT GGC ACA AGA TAT AC-3 '" should read
--5' - AAG ACT GGC ACA AGA TAT AC -3'--.

Column 11,
Line 38, "in by are" should read --in bp are--.

Column 12,
Line 52, "5' -CAA GGC ATT GAT TCA GCA ACA GTG C-3 '" should read
--5'-CAA GGA ATT GAT TCA GCA ACA GTG C - 3'--.

Column 13,
Line 10, "5' – CCT ATT CAC TTG AAT TGA ATC C-3 '" should read
--5' - CCA ATT CAC TTG AAT TGA CGA ATC C - 3'--.

Column 15,
Line 36, "fair" should read --für--.

Signed and Sealed this
Eighth Day of April, 2014

Michelle K. Lee
*Deputy Director of the United States Patent and Trademark Office*